United States Patent [19]

Bardoneschi et al.

[11] 4,165,326
[45] Aug. 21, 1979

[54] STEROIDS AND THEIR PREPARATION

[75] Inventors: Roland Bardoneschi, Vaujours; Alain Jouquey, Paris; Daniel Philibert, La Varenne Saint-Hilaire, all of France

[73] Assignee: Roussel Uclaf, Paris, France

[21] Appl. No.: 891,722

[22] Filed: Mar. 30, 1978

[51] Int. Cl.² .............................................. C07J 9/00
[52] U.S. Cl. ........................ 260/397.5; 260/239.55 R; 260/397.3; 260/397.4
[58] Field of Search ..... Machine Searched Steroids; 260/397.5; 260/239.55

[56] References Cited
FOREIGN PATENT DOCUMENTS
1267915  3/1972  United Kingdom .................. 260/397.4

Primary Examiner—Ethel G. Love
Attorney, Agent, or Firm—Hammond & Littell

[57] ABSTRACT

Steroids of the formula

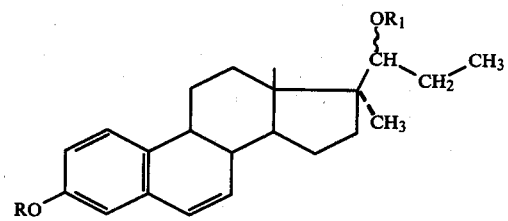

wherein R is selected from the group consisting of hydrogen, alkyl of 1 to 4 carbon atoms, tetrahydropyranyl, trityl and trimethylsilyl, $R_1$ is selected from the group consisting of hydrogen, acryl of an alkanoic acid of 1 to 5 carbon atoms and tetrahyropyranyl and the wavy line indicates that the $OR_1$ group may be in either position about the carbon atom and a process and intermediates for their preparation which compounds are useful as intermediates to form novel tritium compounds of the formula

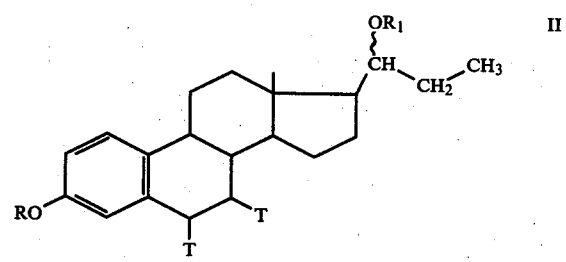

wherein R and $R_1$ have the above definition which are useful as intermediates for the production of $(6,7-H^3)$ $17\alpha,21$-dimethyl-19-nor-$\Delta^{4,9}$-pregnadiene-3,20-dione.

11 Claims, No Drawings

STEROIDS AND THEIR PREPARATION

OBJECTS OF THE INVENTION

It is an object of the invention to provide the novel products of formula I and to provide a novel process for the preparation of the said compounds as well as novel intermediates.

It is another object of the invention to provide the novel tritium steroids of formula II and a process for their preparation.

These and other objects and advantages of the invention will become obvious from the following detailed description.

THE INVENTION

The novel $17\alpha,21$-dimethyl-$\Delta^{1,3,5(10),6}$steroids of the invention have the formula

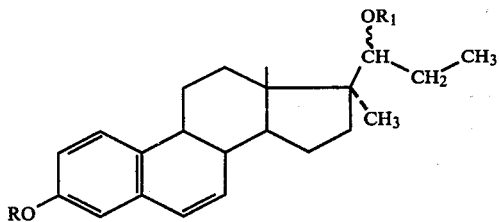

wherein R is selected from the group consisting of hydrogen, alkyl of 1 to 4 carbon atoms, tetrahydropyranyl, trityl and trimethylsilyl, $R_1$ is selected from the group consisting of hydrogen, acyl of an alkanoic acid of 1 to 5 carbon atoms and tetrahydropyranyl and the wavy line indicates that the $OR_1$ group may be in either position about the carbon atoms.

Specific alkyl examples for R are methyl, ethyl, propyl, isopropyl, butyl, sec-butyl and tert.-butyl. Specific examples of alkanoic acids from which $R_1$ may be derived are formic acid, acetic acid, propionic acid, butyric acid and valeric acid.

Specific preferred compounds of formula I are $17\alpha,21$-dimethyl-19-nor-$\Delta^{1,3,5(10),6}$-pregnatetraene-3,20$\xi$-diol, 3-methoxy-$17\alpha,21$-dimethyl-19-nor-$\Delta^{1,3,5(10),6}$-pregnatetraene-20$\xi$-ol, 3-methoxy-20$\xi$-acetoxy-$17\alpha,21$-dimethyl-19-nor-$\Delta^{1,3,5(10)6}$-pregnatetraene and $17\alpha,21$-dimethyl-20$\xi$-acetoxy-19-nor-$\Delta^{1,3,5(10,6}$-pregnatetraene-3-ol.

The novel process of the invention for the preparation of the compounds of formula I comprises reacting 3-methoxy-$17\alpha$-methyl-19-nor-$\Delta^{1,3,5(10)}$-pregnatriene-20-one with a methyl halide to obtain 3-methoxy-$17\alpha,21$-dimethyl-19-nor-$\Delta^{1,3,5(10)}$-pregnatriene-20-one, reacting the latter with a reducing agent to form 3-methoxy-$17\alpha,21$-dimethyl-19-nor-$\Delta^{1,3,5(10)}$-pregnatriene-20$\xi$-ol, subjecting the latter to the Birch reaction with lithium in ammonia to form $17\alpha,21$-dimethyl-19-nor-$\Delta^{5(10)}$-pregnene-20$\xi$-ol-3-one, isomerizing the latter with a strong acid to form $17\alpha,21$-dimethyl-19-nor-$\Delta^4$-pregnene-20$\xi$-ol-3-one, reacting the latter with an etherification or esterification agent to obtain $17\alpha,21$-dimethyl-20$\xi$-$OR_1'$-19-nor-$\Delta^4$-pregnene-3-one wherein $R_1'$ is acyl of an alkanoic acid of 1 to 5 carbon atoms or tetrahydropyranyl, reacting the latter with a halogenation agent to form 2,6-dihalo-$17\alpha,21$-dimethyl-20$\xi$-$OR_1'$-19-nor-$\Delta^4$-pregnene-3-one, subjecting the latter to deshalohydration with an alkali metal halide in dimethylformamide to form $17\alpha,21$-dimethyl-20$\xi$-$OR_1'$-19-nor-$\Delta^{1,3,5(10)6}$-pregnatetraene-3-one, reacting the latter with an alkylation agent selected from the group consisting of dihydropyran, tritylchloride and trimethylsilyl chloride to obtain the corresponding compound of formula I wherein R and $R_1$ are other than hydrogen and the latter may be reacted with an acid or a base to obtain the corresponding compound of formula I wherein $R_1$ is hydrogen and then optionally with an acid to obtain the compound of formula I wherein R and $R_1$ are both hydrogen.

In a preferred mode of the process of the invention, the 21-methylation is effected with methyl iodide in the presence of a tertiary base such as potassium tert.-butylate and the reaction is effected in toluene. The preferred reducing agent for reducing the 20-keto group is an alkali metal borohydride such as sodium borohydride and the Birch reaction is preferably effected in ethanol. The preferred strong acid for the isomerization of the double bond is hydrochloric acid in ethanol and the preferred esterification agent is a functional derivative of acetic acid such as acetic anhydride in pyridine while the preferred esterification agent is dihydropyran. The preferred halogenation agent is bromine in acetic acid in the presence of ether and the deshalogenation is effected with lithium chloride. The blocking agent for the 3-hydroxyl group is preferably dimethylsulfate in the presence of sodium hydroxide, dihydropyran, tritylchloride or trimethylsilyl chloride. The hydrolysis to free the 20$\xi$ hydroxy group may be effected with a base such as alcoholic sodium hydroxide or potassium hydroxide or with an acid such as acetic acid. The acid hydrolysis to obtain the 3-hydroxyl group is preferably effected with aqueous acetic acid or a hydrogen halide such as hydrochloric acid.

Among the novel intermediates of the invention formed in the process are 3-methoxy-$17\alpha,21$-dimethyl-19-nor-$\Delta^{1,3,5(10)}$-pregnatriene-20-one, 3-methoxy-$17\alpha,21$-dimethyl-19-nor-$\Delta^{1,3,5(10)}$-pregnatriene-20$\xi$-ol, $17\alpha,21$-dimethyl-19-nor-$\Delta^{5(10)}$-pregnene-20$\xi$-ol-3-one, $17\alpha,21$-dimethyl-19-nor-$\Delta^4$-pregnene-20$\xi$-ol-3-one, $17\alpha,21$-dimethyl-20$\xi$-acetoxy-19-nor-$\Delta^4$-pregnene-3-one and 2,6-dibromo-$17\alpha,21$-dimethyl-20$\xi$-acetoxy-19-nor-$\Delta^4$-pregnene-3-one.

The novel process of the invention for the preparation of $(6,7$-$H^3)$ 3-OR-$17\alpha,21$-dimethyl-20$\xi$-$OR_1$-19-nor-$\Delta^{2,5(10)}$-pregnadienes comprises reacting a compound of formula I with tritium hydrogen in the presence of a catalyst to form the corresponding $(6,7$-$H^3)$ 3-OR-$17\alpha,21$-dimethyl-20$\xi$-$OR_1$-19-nor-$\Delta^{1,3,5(10)}$-pregnatriene and when R is methyl, reacting the latter with lithium in ammonia in the presence of ethanol according to the Birch reaction to obtain when $R_1$ is hydrogen or acyl of an alkanoic acid of 1 to 5 carbon atoms $(6,7$-$H^3)$ 3-methoxy-$17\alpha,21$-dimethyl-19-nor-$\Delta^{2,5(10)}$-pregnadiene-20$\xi$-ol or when $R_1$ is tetrahydropyranyl $(6,7$-$H^3)$ 3-methoxy-$17\alpha,21$-dimethyl-20$\xi$-tetrahydropyranyloxy-19-nor-$\Delta^{2,5(10)}$-pregnadiene or when R is other than methyl or hydrogen and $R_1$ is other than hydrogen, reacting the said product with an acid such as acetic acid or a hydrogen halide such as hydrochloric acid to form $(6,7$-$H^3)$ $17\alpha,21$-dimethyl-20$\xi$-$OR_1$-19-nor-$\Delta^{1,3,5(10)}$-pregnatriene-3-ol, treating the latter with a methylation agent such as dimethylsulfate to obtain $(6.7$-$H^3)$ 3-methoxy-$17\alpha,21$-dimethyl-20$\xi$-$OR_1$-19-nor-$\Delta^{1,3,5(10)}$-pregnatriene and subjecting the latter to the Birch reaction with lithium in ammonia in the presence of ethanol to obtain when $R_1$ is hydrogen or acyl of an alkanoic acid $(6,7$-$H^3)$ 3-methoxy-$17\alpha,21$- dimethyl-19-nor-$\Delta^{2,5(10)}$-pregnadiene-20$\xi$-ol or when $R_1$ is tetrahydropyranyl (6,7-$H^3$) 3-methoxy-17$\alpha$,21-dimethyl-20$\xi$-tetrahydropyranyloxy-19-nor-$\Delta^{2,5(10)}$-pregnadiene.

(6,7-$H^3$) 3-methoxy-17$\alpha$,21-dimethyl-19-nor-$\Delta^{2,5(10)}$-pregnadiene-20$\xi$-ol is useful as described in commonly assigned, copending U.S. patent application Ser. No. 855,177 filed Nov. 28, 1977 for the preparation of (6,7-$H^3$) 17$\alpha$,21-dimethyl-19-nor-$\Delta^{4,9}$-pregnadiene-3,20-dione by reacting (6,7-$H^3$) 3-methoxy-17$\alpha$,21-dimethyl-19-nor-$\Delta^{2,5(10)}$-pregnadiene-20$\xi$-ol with an aqueous weak acid such as acetic acid to obtain (6,7-$H^3$) 17$\alpha$,21-dimethyl-19-nor-$\Delta^{5(10)}$-pregnene-20$\xi$-ol-3-one, reacting the latter with pyridine perbromide to obtain (6,7-$H^3$) 17$\alpha$,21-dimethyl-19-nor-$\Delta^{4,9}$-pregnadiene-20$\xi$-ol-3-one and reacting the latter with aqueous sulfochromic acid to obtain (6,7-$H^3$) 17$\alpha$,21-dimethyl-19-nor-$\Delta^{4,9}$-pregnadiene-3,20-dione.

The use of 17$\alpha$,21-dimethyl-(6,7-$H^3$)-19-nor-$\Delta^{4,9}$-pregnadiene-3,20-dione for the characterization of progesterone reception is described in numerous publications such as Raynaud et al. [Steroids, July 1973, p. 89–97] and the said product has a specific activity on the order of 50 Ci/mM. The said product permits the dosage of specific receptor of progesterone in uterine cytosol or in the cycloplasma of tumor cells (cancer) and in induced tumors provoked by DMBA (9,10-dimethyl-1,2-benzathracene) in the rat. The product has the advantage compared to progesterone that it is not fixed by transcortine and has an affinity for the reception of progesterone 6 to 8 times greater than the affinity for the latter.

The novel tritium intermediates products of the invention have the formula

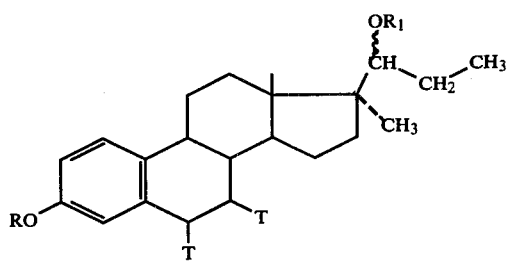

II wherein R and $R_1$ have the above definitions and T indicates a tritium hydrogen. Especially preferred is (6,7-$H^3$) 3-methoxy-17$\alpha$,21-dimethyl-19-nor-$\Delta^{1,3,5(10)}$-pregnatriene-20$\xi$-ol.

The starting material for the process to prepare the compounds of formula I, namely 3-methoxy-17$\alpha$-methyl-19-nor-$\Delta^{1,3,5(10)}$-pregnatriene-20-one, is described in French Pat. No. 1,480,247.

In the following examples there are described several preferred embodiments to illustrate the invention. However, it is to be understood that the invention is not intended to be limited to the specific embodiments.

EXAMPLE 1

3-methoxy-17$\alpha$,21-dimethyl-19-nor-$\Delta^{1,3,5(10),6}$-pregnatetraene-20$\xi$-ol

STEP A:

3-methoxy-17$\alpha$,21-dimethyl-19-nor-$\Delta^{1,3,5(10)}$-pregnatriene-20-one 126 g of potassium tert.-butylate were added under an inert atmosphere with stirring over 15 minutes to 1840 ml of toluene and then a mixture of 306 g of 17$\alpha$-methyl-19-nor-$\Delta^{1,3,5(10)}$-pregnatriene-20-one in 900 ml of toluene was added thereto over 15 minutes. The mixture was rinsed with 300 ml of toluene and was then stirred at room temperature for one hour and was cooled to 0° C. 600 ml of methyl iodide were added to the mixture at 0° C. and the mixture was stirred at 0° C. for 20 hours. 6000 ml of water were added thereto and the aqueous phase was separated and extracted several times with chloroform. The combined extracts were washed with water, dried over sodium sulfate and evaporated to dryness under reduced pressure to obtain 312 g of 3-methoxy-17$\alpha$,21-dimethyl-19-nor-$\Delta^{1,3,5(10)}$-pregnatriene-20-one which after chromatography over silica gel and elution with a 5-3.5-1.5 cyclohexane-benzene-ethyl acetate mixture melted at $\approx$97° C. The product was used as is for the next step.

STEP B:

3-methoxy-17$\alpha$,21-dimethyl-19-nor-$\Delta^{1,3,5(10)}$-pregnatriene-20$\xi$-ol 60 g of the product of Step A and 17.5 g of sodium borohydride were added with stirring at room temperature to 300 ml of ethanol and 90 ml of water and the reaction mixture was refluxed for about 5 hours with stirring. The mixture was cooled to 50° C. and was poured with stirring into 900 ml of water. The mixture was vacuum filtered and the crystals were washed with water and dried to obtain 59.6 g of 3-methoxy-17$\alpha$,21-dimethyl-19-nor-$\Delta^{1,3,5(10)}$-pregnatriene-20$\xi$-1-ol which after chromatography over silica gel and elution with a 7-3 cyclohexane-ethylacetate mixture melted at =70° C. The product was used as is for the next step.

STEP C:

17$\alpha$,21-dimethyl-19-nor-$\Delta^{5(10)}$-pregnene-20$\xi$-ol-3-one

A solution of 85 g of the product of Step B in 850 ml of tetrahydrofuran was added over 40 minutes at −40° C. to 1400 ml of ammonia and 42 ml of ethanol were added thereto at −40° C. under an inert atmosphere. Then, 8.940 g of lithium were added to the mixture over 40 minutes and the reaction mixture was stirred at -40 C. for 15 minutes. The ethanol and lithium addition operation was repeated two more times and the mixture was then added to 127.5 ml of ethanol. The ammonia was distilled under an inert atmosphere at a temperature below 15° C. and then 850 ml of water were added. The mixture was stirred for one hour and then allowed to stand for 20 hours under an inert atmosphere at 20° C. The mixture was vacuum filtered and the product was rinsed with ether. The filtrate was distilled to dryness under reduced pressure and the residue was taken up in 85 ml of tetrahydrofuran. 255 ml of acetic acid were added to the mixture which was then stirred for one hour at 20° C. under an inert atmosphere and was then poured into a water-ice-ammonium hydroxide mixture. The mixture was vacuum filtered. The precipitate was washed with water and was taken up in 850 ml of ether. The ether solution was dried over sodium sulfate and was evaporated to dryness under reduced pressure. The residue was empasted with stirring with 170 ml of petroleum ether (b.p.=64°–75° C.), was vacuum filtered and dried to obtain 70.7 g of 17$\alpha$,21-dimethyl-19-nor-$\Delta^{5(10)}$-pregnene-20$\xi$-ol-3-one with a melting point of =129° C. which was used as is for the next step.

STEP D:

17α,21-dimethyl-19-nor-Δ⁴-pregnene-20ξ-ol-3-one 7.9 ml of 1N hydrochloric acid were added to a solution of 7.85 g of the product of Step C in 78.5 ml of methanol and the mixture was refluxed for 1 hour and then was cooled. The mixture was vacuum filtered and the precipitate was washed with methanol and with petroleum ether (b.p.=40°–70° C.) and dried under reduced pressure to obtain 6.68 g of 17α,21-dimethyl-19-nor-Δ⁴-pregnene-20ξ-ol-3-one which after chromatography over silica gel and elution with a 9-1 methylene chloride-ethylacetate mixture melted at 221° C.

STEP B:

17α,21-dimethyl-20ξ-acetoxy-19-nor-Δ⁴-pregnene-3-one

A mixture of 6.68 g of the product of Step D, 33.5 ml of pyridine and 16.5 ml of acetic anhydride was stirred at 70° C. for 24 hours and was then poured into a mixture of 200 ml of 1N hydrochloric acid and ice. The mixture was extracted several times with methylene chloride and the organic extracts were washed with 1N hydrochloric acid, with water and finally with an aqueous saturated sodium bicarbonate solution, was dried over sodium sulfate and treated with activated carbon and alumina. The mixture was filtered and the filtrate was evaporated to dryness under reduced pressure. The residue was taken up in isopropyl ether and the mixture was vacuum filtered. The product was dried under reduced pressure to obtain 6.3 g of 17α,21-dimethyl-20ξ-acetoxy-19-nor-Δ⁴-pregnene-3-one which was chromatographed over silica gel and was eluted with a 95-5 methylene chloride-ethylacetate mixture. The product was crystallized from a methylene chloride-isopropyl ether mixture to obtain a product with a melting point of 222° C.

Analysis: $C_{24}H_{38}O_3$. Calculated: %C 77.37; %H 9.74. Found: %C 76.9, %H 9.7.

STEP F:

2,6-dibromo-17α,21-dimethyl-20ξ-acetoxy-19-nor-Δ⁴-pregnene-3-one 27 ml of a solution of 15.6% of bromine in acetic acid were slowly added at 15° C. to a suspension of 4.88 of the product of Step E in 50 ml of ether and the mixture was stirred for 15 minutes at about 15° C. and was poured into 100 ml of methylene chloride. The mixture was added to water and the organic phase was washed with an aqueous sodium bicarbonate solution, then with water, dried over sodium sulfate and filtered to obtain a solution of 2,6-dibromo-20ξ-acetoxy-17α,21-dimethyl-19-nor-Δ⁴-pregnene-3-one which was used as is for the next step.

STEP G:

17α,21-dimethyl-20ξ-acetoxy-19-nor-Δ$^{1,3,5(10),6}$-pregnatetraene-3-ol

A mixture of 4.88 g of lithium chloride in 50 ml of dimethylformamide was heated in an oil bath to 120° C. and the solution of Step F was added thereto over about 35 minutes while distilling. After the methylene chloride was removed, the mixture was held at 100° C. for 15 minutes and was then cooled to room temperature. Methylene chloride was added thereto and the mixture was poured into water. The organic phase was washed with a saturated aqueous sodium bicarbonate solution and then with water. The wash waters were extracted with methylene chloride and the combined organic phases were dried over sodium sulfate and evaporated to dryness under reduced pressure. The residue was taken up in methanol and was chromatographed over silica gel. Elution with a 95-5 methylene chloride-isopropyl ether mixture yielded 2.65 g of 17α,21-dimethyl-20ξ-acetoxy-19-nor-Δ$^{1,3,5(10),6}$-pregnatetraene-3-ol melting at 246° C.

STEP H:

3-methoxy-17α,21-dimethyl-20ξ-acetoxy-19-nor-Δ$^{1,3,5(10),6}$-pregnatetraene 13 ml of 1N sodium hydroxide, 1.45 ml of methyl sulfate and 190 mg of tetrabutyl ammonium chloride were added at 20° C. to a mixture of 1.92 g of the product of Step F and 29 ml of methylene chloride and after stirring at 20° C. for 3 hours, the mixture was poured into 100 ml of 0.1N sodium hydroxide solution. The mixture was extracted several times with methylene chloride and the combined organic phases were washed with hydrochloric acid and water, dried over sodium sulfate and evaporated to dryness. The residue was taken up in isopropyl ether and the solution was concentrated and cooled and vacuum filtered. The product was washed with isopropyl ether and dried under reduced pressure to obtain 1.87 g of 3-methoxy-17α,21-dimethyl-20ξ-acetoxy-19-nor-Δ$^{1,3,5(10),6}$-prenatetraene melting at 162° C. The product was purified by chromatography over silica gel and elution with an 85-15 cyclohexane-ethyl acetate mixture.

STEP I:

3-methoxy-17α,21-dimethyl-19-nor-Δ$^{1,3,5(10),6}$-pregnatetraene-20ξ-ol

A mixture of 1.87 g of the product of Step H and 7.5 ml of 3N ethanoics potassium hydroxide was refluxed for 6 hours and was then poured into 30 ml of water. The mixture was extracted several times with methylene chloride and the combined organic phase was washed with hydrochloric acid and with water and dried over sodium sulfate. The solution was treated with alumina and was filtered and the filtrate was evaporated to dryness under reduced pressure. The residue was taken up in isopropyl ether and the solution was cooled and vacuum filtered. The product was washed with isopropyl ether and was dried under reduced pressure to obtain 1.13 g of raw product. The latter was chromatographed over silica gel and was eluted with a 9-1 cyclohexane-ethyl acetate mixture to obtain 3-methoxy-17α,21-dimethyl-19-nor-Δ$^{1,3,5,(10),6}$-pregnatetraene-20ξ-ol melting at 141° C.

EXAMPLE 2

(6,7H³) 3-methoxy 17α,21-dimethyl-19-nor-Δ$^{2,5(10)}$-pregnadiene-20ξ-ol

STEP A:

(6,7-H³) 3-methoxy-17α,21-dimethyl-19-nor-Δ$^{1,3,5(10)}$-pregnatriene-20ξ-ol

A mixture of 65 mg of 3-methoxy-17α,21-dimethyl-19-nor-Δ$^{1,3,5(10),6}$-pregnatetraene-20ξ-ol, 20 ml of palladized carbon and 2.5 ml of ethyl acetate was cooled with liquid nitrogen and 7.95 ml of tritium with an activity of 20 Ci were added thereto under reduced pressure. The temperature was allowed to return to room temperature and the mixture was stirred for 3 hours and was then again cooled with liquid nitrogen to recover excess tritium. The temperature again was allowed to return to room temperature and the mixture was filtered to remove the catalyst which was washed with ethyl acetate. The filtrate was evaporated to dryness under reduced pressure to obtain 65 mg of raw resin. The latter was chromatographed over silica gel and was eluted with a 1-1 methylene chloride-acetone mixture. The eluate was filtered and the filtrate was evaporated to dryness. The residue was taken up in a 10-1 benzene-ethyl acetate mixture and the solution was evaporated to obtain 55 mg of (6,7-$H^3$) 3-methoxy-17α,21-dimethyl-19-nor-$\Delta^{1,3,5(10)}$-pregnatriene-20ξ-ol with a Rf=0.38 and a specific activity of 56.5 Ci/mmol.

STEP B:

(6,7-$H^3$)
3-methoxy-17α,21-dimethyl-19-nor-$\Delta^{2,5(10)}$-pregnadiene-20ξ-ol 25 ml of liquid ammonia solution (cooled to −35 to −40° C.) were admixed with a solution of 55 mg of (6,7-$H^3$) 3-methoxy-17α,21-dimethyl-19-nor-$\Delta^{1,3,5(10)}$-pregnatriene-20ξ-ol in 5 ml of tetrahydrofuran and 0.5 ml of ethanol and 200 mg of lithium were added thereto in small fractions. The mixture was stirred for about 1 hour at −35° C. and then 10 ml of ethanol were slowly added thereto. The ammonia was removed by letting the temperature rise to room temperature and 50 ml of water were added thereto. The mixture was extracted several times with benzene and the combined organic phases were dried over sodium sulfate and were evaporated to dryness under reduced pressure to obtain 55 mg of a resin which was (6,7-$H^3$) 3-methoxy-17α,21-dimethyl-19-nor-$\Delta^{2,5(10)}$-pregnadiene-20ξ-ol which was used for the synthesis of (6,7-$H^3$) 17α,21-dimethyl-19-nor-$\Delta^{4,9(10)}$-pregnadiene-3,20-dione. The product was purified by chromatography over silica gel and elution with a 10-1 benzene-ethyl acetate mixture to obtain a product with a Rf=0.38 and which was identical to that described in copending U.S. patent application Ser. No. 855,177 filed Nov. 28 1977.

Various modifications of the products and process of the invention may be made without departing from the spirit or scope thereof and it is to be understood that the invention is to be limited only as defined in the appended claims.

We claim:
1. A compound of the formula

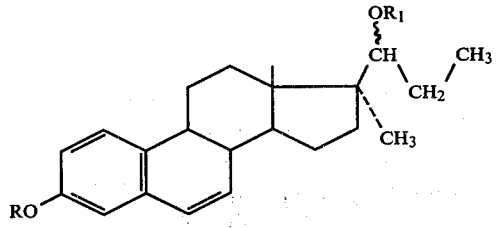

wherein R is selected from the group consisting of hydrogen, alkyl of 1 to 4 carbon atoms, tetrahydropryanyl, trityl and trimethylsilyl, $R_1$ is selected from the group consisting of hydrogen, acyl of an alkanoic acid of 1 to 5 carbon atoms and tetrahydropyranyl and the wavy line indicates that the $OR_1$ group may be in either position about the carbon atoms.

2. A compound of claim 1 which is 17α,21-dimethyl-19-nor-$\Delta^{1,3,5(10),6}$-pregnatetraene-3,20ξ-diol.

3. A compound of claim 1 which is 3-methoxy-17α,21-dimethyl-19-nor-$\Delta^{1,3,5(10),6}$-prenatetraene-20ξ-ol.

4. A compound of claim 1 which is 3-methoxy-17α,21-dimethyl-20ξ-acetoxy-19-nor-$\Delta^{1,3,5(10),6}$-prenatetraene.

5. A compound of claim 1 which is 17α,21-dimethyl-20ξ-acetoxy-19-nor-$\Delta^{1,3,5(10),6}$-pregnatetraene-3-ol.

6. A process for the preparation of a compound of claim 1 comprising reacting 3-methoxy-17α-methyl-19-nor-$\Delta^{1,3,5(10)}$-pregnatriene-20-one with a methyl halide to obtain 3-methoxy-17α,21-dimethyl-19-nor-$\Delta^{1,3,5(10)}$-pregnatriene-20-one, reacting the latter with a reducing agent to form 3-methoxy-17α,21-dimethyl-19-nor-$\Delta^{1,3,5(10)}$-pregnatriene-20ξ-ol, subjecting the latter to the Birch reaction with lithium in ammonia to form 17α,21-dimethyl-19-nor-$\Delta^{5(10)}$-pregnene-20ξ-ol-3-one, isomerizing the latter with a strong acid to form 17α,21-dimethyl-19-nor-$\Delta^4$-pregnene-20ξ-ol-3-one, reacting the latter with an etherification or esterification agent to obtain 17α,21-dimethyl-20ξ-$OR_1'$-19-nor-$\Delta^4$-pregnene-3-one wherein $R_1'$ is acyl of an alkanoic acid of 1 to 5 carbon atoms or tetrahydropyranyl, reacting the latter with a halogenation agent to form 2,6-dihalo-17α,21-dimethyl-20ξ-$OR_1'$-19-nor-$\Delta^4$-pregnene-3-one, subjecting the latter to deshalohydration with an alkali metal halide in dimethylformamide to form 17α,21-dimethyl-20ξ-$OR_1'$-19-nor-$\Delta^{1,3,5(10),6}$-pregnatetraene-3-one, reacting the latter with an alkylation agent selected from the group consisting of dihydropyran, trityl chloride and trimethylsilyl chloride to obtain the corresponding compound of claim 1 wherein R and $R_1$ are other than hydrogen and the latter may be reacted with an acid or a base to obtain the corresponding compound of claim 1 wherein $R_1$ is hydrogen and then optionally with an acid to obtain the compound of claim 1 wherein R and $R_1$ are both hydrogen.

7. The process of claim 1 wherein the methylation of the 21-position is effected with methyl iodide in the presence of a tertiary base in toluene, the halogenation is effected with bromine in acetic acid in ether and the alkali metal halide is lithium chloride.

8. A compound selected from the group consisting of 3-methoxy-17α,21-dimethyl-19-nor-$\Delta^{1,3,5(10)}$-pregnatriene-20-one, 3-methoxy-17α,21-dimethyl-19-nor-$\Delta^{1,3,5(10)}$-pregnatriene -20ξ-ol, 17α,21-dimethyl-19-nor-$\Delta^{5(10)}$-pregnene-20ξ-ol-3-one, 17α,21-dimethyl-19-nor-$\Delta^4$-pregnene-20ξ-ol-3-one, 17α,21-dimethyl-20ξ-acetoxy-19-nor-$\Delta^4$-pregnene-3-one and 2,6-dibromo-17α,21-dimethyl-20ξ-acetoxy-19-nor-$\Delta^4$-pregnene-3-one.

9. A tritium compound of the formula

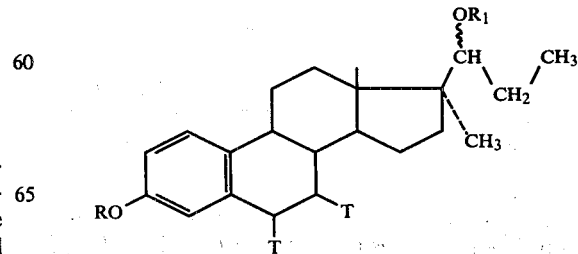

wherein R is selected from the group consisting of hydrogen, alkyl of 1 to 4 carbon atoms, tetrahydropyranyl, trityl and trimethylsilyl, $R_1$ is selected from the group consisting of hydrogen, acyl of an alkanoic acid of 1 to 5 carbon atoms and tetrahydropyranyl, the wavy line means that the $OR_1$ group may be in either position about the carbon atoms.

10. A compound of claim 9 which is $(6,7-H^3)$ 3-methoxy-17α,21-dimethyl-19-nor-$\Delta^{1,3,5(10)}$pregnatriene-20ξ-ol.

11. A process for the preparation of $(6,7-H^3)$ 3-OR-17α,21-dimethyl-20ξ-$OR_1$-19-nor-$\Delta^{2,5(10)}$-pregnadiene wherein R is selected from the group consisting of hydrogen, alkyl of 1 to 4 carbon atoms, tetrahydropyranyl, trityl and trimethylsilyl, $R_1$ is selected from the group consisting of hydrogen, acyl of an alkanoic acid of 1 to 5 carbon atoms, and tetrahydropyranyl, the wavy line means that the $OR_1$ group may be in either position about the carbon atoms comprising reacting a compound of claim 1 with tritium hydrogen in the presence of a catalyst to form the corresponding $(6,7-H^3)$ 3-OR-17α,21-dimethyl-20ξ-$OR_1$-19-nor-$\Delta^{1,3,5(10)}$-pregnatriene and when R is methyl, reacting the latter with lithium in ammonia in the presence of ethanol according to the Birch reaction to obtain when $R_1$ is hydrogen or acyl of an alkanoic acic of 1 to 5 carbon atoms $(6,7-H^3)$ 3-methoxy-17α,21-dimethyl-19-nor-$\Delta^{2,5(10)}$-pregnadiene-20ξ-ol or when $R_1$ is tetrahydropyranyl $(6,7-H^3)$ 3-methoxy-17α,21-dimethyl-20ξ-tetrahydropyranyloxy-19-nor-$\Delta^{2,5(10)}$-pregnadiene or when R is other than methyl or hydrogen and $R_1$ is other than hydrogen, reacting the said product with an acid such as acetic acid or a hydrogen halide such as hydrochloric acid to form $(6,7-H^3)$ 17α,21-dimethyl-20ξ-$OR_1$-19-nor$\Delta^{1,3,5(10)}$-pregnatriene-3-ol, treating the latter with a methylation agent such as dimethyl sulfate to obtain $(6,7-H^3)$ 3-methoxy-17α,21-dimethyl-20ξ-$OR_1$-19-nor-$\Delta^{1,3,5(10)}$-pregnatriene and subjecting the latter to the Birch reaction with lithium in ammonia in the presence of ethanol to obtain when $R_1$ is hydrogen or acyl of an alkanoic acid $(6,7-H^3)$ 3-methoxy-17α,21-dimethyl-19-nor-$\Delta^{2,5(10)}$-pregnadiene-20ξ-ol or when $R_1$ is tetrahydropyranyl $(6.7-H^3)$ 3-methoxy-17α,21-dimethyl-20ξ-tetrahydropyranyloxy-19-nor-$\Delta^{2,5(10)}$-pregadiene.

* * * * *